United States Patent
Li et al.

(10) Patent No.: US 10,510,981 B2
(45) Date of Patent: Dec. 17, 2019

(54) ORGANIC LIGHT-EMITTING DIODE DISPLAY PANEL, FABRICATION METHOD, AND ELECTRONIC APPARATUS

(71) Applicant: Shanghai Tianma AM-OLED Co., Ltd., Shanghai (CN)

(72) Inventors: Jie Li, Shanghai (CN); Yuji Hamada, Shanghai (CN); Xiangcheng Wang, Shanghai (CN); Jinghua Niu, Shanghai (CN); Huihui Ma, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 0 days.

(21) Appl. No.: 15/605,537

(22) Filed: May 25, 2017

(65) Prior Publication Data

US 2017/0263884 A1    Sep. 14, 2017

(30) Foreign Application Priority Data

Mar. 22, 2017   (CN) .......................... 2017 1 0174864

(51) Int. Cl.
*H01L 51/52* (2006.01)
*H01L 51/56* (2006.01)
(Continued)

(52) U.S. Cl.
CPC ........ *H01L 51/5237* (2013.01); *C07C 211/54* (2013.01); *C07C 255/58* (2013.01);
(Continued)

(58) Field of Classification Search
CPC ............. H01L 51/5237; H01L 51/0059; H01L 51/5056; H01L 51/5072; C07C 211/54
See application file for complete search history.

(56) References Cited

U.S. PATENT DOCUMENTS 4,925,759 A * 5/1990 Hanatani .............. G03G 5/0614
430/58.8
5,272,031 A * 12/1993 Hanatani ............... C07C 211/54
430/58.8
(Continued)

FOREIGN PATENT DOCUMENTS

CN    102820433 A    12/2012
CN    203339167 U    12/2013

*Primary Examiner* — Tuan A Hoang
(74) *Attorney, Agent, or Firm* — Anova Law Group PLLC

(57) ABSTRACT

An organic light-emitting diode (OLED) display panel, a fabrication method thereof, and an electronic apparatus including the OLED display panel are provided. The OLED display panel comprises: a substrate, an organic light-emitting device, and a capping layer. A material of the capping layer includes a compound of a chemical formula (I),

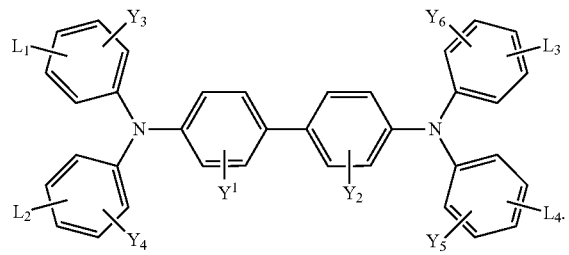

L1, L2, L3, and L4 are independently selected from a hydrogen atom, a substituted or -unsubstituted alkyl, a substituted or unsubstituted alkenyl, a substituted or unsubstituted alkynyl, and a substituted or unsubstituted phenyl. A total quantity of benzene rings included in L1, L2, L3, and L4 is from 0 to 6. Y1, Y2, Y3, Y4, Y5, and Y6 are independently selected from a hydrogen atom, a substituted (Continued)

or unsubstituted alkyl, a substituted of unsubstituted alkenyl, and a substituted or unsubstituted alkynyl.

21 Claims, 4 Drawing Sheets

(51) Int. Cl.
    *H01L 51/00*     (2006.01)
    *C07C 211/54*     (2006.01)
    *C07C 255/58*     (2006.01)

(52) U.S. Cl.
    CPC ...... *H01L 51/0059* (2013.01); *H01L 51/5253* (2013.01); *H01L 51/56* (2013.01)

(56) References Cited

U.S. PATENT DOCUMENTS

| | | | | |
|---|---|---|---|---|
| 5,550,290 | A * | 8/1996 | Mizuta | C07C 211/54 564/309 |
| 6,106,352 | A * | 8/2000 | Fujii | H01L 27/3244 445/24 |
| 8,586,969 | B2 * | 11/2013 | Murata | H01L 51/5088 257/40 |
| 2004/0062947 | A1 * | 4/2004 | Lamansky | H01L 51/5012 428/690 |
| 2010/0171105 | A1 | 7/2010 | Kim et al. | |
| 2014/0225100 | A1 * | 8/2014 | Yokoyama | C07D 213/38 257/40 |
| 2015/0060797 | A1 * | 3/2015 | Lee | H01L 51/0003 257/40 |
| 2018/0212192 | A1 * | 7/2018 | Jin | H01L 51/5246 |
| 2018/0331298 | A1 * | 11/2018 | Hayashi | C09K 11/06 |

* cited by examiner

ORGANIC LIGHT-EMITTING DIODE DISPLAY PANEL, FABRICATION METHOD, AND ELECTRONIC APPARATUS

CROSS-REFERENCES TO RELATED APPLICATIONS

This application claims priority of Chinese Patent Application No. 201710174864.9, filed on Mar. 22, 2017, the entire contents of which are hereby incorporated by reference.

FIELD OF THE DISCLOSURE

The present disclosure generally relates to the field of flexible organic electroluminescent devices and, more particularly, relates to an organic light-emitting diode (OLED) display panel, a fabrication method thereof, and an electronic apparatus including the OLED display panel.

BACKGROUND

In an organic electroluminescent device, such as an OLED, a significant difference often exists between the external quantum efficiency and the internal quantum efficiency of organic electroluminescence, which substantially limits the development of OLEDs. The existing technology in the field can improve the external quantum efficiency of OLEDs by adding a capping layer, through which the luminous efficiency is increased by more than 30%.

The capping layer adopted in the existing technology often includes an inorganic layer or an organic layer. The inorganic layer is able to prevent moisture and oxygen from intruding into the OLED devices (e.g. OLED display panels) to a certain extent. Pixel shrinkage tests show that, an OLED device with an inorganic capping layer is subjected to a reduced erosion effect of moisture and oxygen on the light-emitting areas as compared to an OLED device without the inorganic capping layer. However, the inorganic capping layer has to be deposited by chemical vapor deposition (CVD) with strict deposition requirements. In addition, the inorganic capping layer has a low light extraction efficiency.

When the conventional inorganic layer in the capping layer is replaced with an organic layer, because of the substantially large refractive index n of the organic layer, the light extraction efficiency of the capping layer may be improved. However, when an organic layer is adopted as the capping layer and prepared using an inkjet printing (IJP) technique, the lifetime of the OLED device may be degraded. Thus, an OLED display panel, whose capping layer can be prepared using the inkjet printing (IJP) technique and, meanwhile, the light extraction efficiency is substantially high while the lifetime is not degraded, is highly desired in the field.

Further, when fabricating the capping layer including the organic layer, the surface of the fabricated capping layer may be uneven, showing bumps and hollows. An OLED display panel having a smooth capping layer is desired in the field.

The disclosed OLED display panel, fabrication method thereof, and electronic apparatus including the OLED display panel are directed to solve one or more problems set forth above and other problems.

BRIEF SUMMARY OF THE DISCLOSURE

One aspect of the present disclosure provides an organic light-emitting diode (OLED) display panel. The OLED display panel comprises a substrate; an organic light-emitting device comprising a first electrode, an organic light-emitting layer, and a second electrode, successively disposed on one side of the substrate, wherein the second electrode has a first side facing toward the substrate and an opposing side; and a capping layer disposed on the opposing side of the second electrode, wherein a material of the capping layer includes a compound of a chemical formula (I):

chemical formula (I)

L1, L2, L3, and L4 are independently selected from a hydrogen atom, a substituted or unsubstituted alkyl, a substituted or unsubstituted alkenyl, a substituted of unsubstituted alkynyl, and a substituted or unsubstituted phenyl. A total quantity of benzene rings included in L1, L2, L3, and L4 is from 0 to 6. Y1, Y2, Y3, Y4, Y5, and Y6 are independently selected from a hydrogen atom, a substituted or unsubstituted alkyl, a substituted or unsubstituted alkenyl, and a substituted or unsubstituted alkynyl.

Another aspect of the present disclosure provides a fabrication method for an OLED display panel. The fabrication method comprises: providing a substrate; forming an organic light-emitting device on the substrate, wherein the organic light-emitting device comprises a first electrode, an organic light-emitting layer, and a second electrode, and the second electrode has a first side facing toward the substrate and an opposing side; and forming a capping layer on the opposing side of the second electrode, wherein the capping layer is formed by dissolving a compound of a chemical formula (I) in a solvent to form an inkjet solution, inkjet printing the inkjet solution as a film onto a surface of the organic light-emitting device, wherein: the compound has the chemical formula (I):

chemical formula (I)

L1, L2, L3, and L4 are independently selected from a hydrogen atom, a substituted or unsubstituted alkyl, a substituted or unsubstituted alkenyl, a substituted or unsubstituted alkynyl, and a substituted or unsubstituted phenyl. A total quantity of benzene rings included in L1, L2, L3, and L4 is from 0 to 6. Y1, Y2, Y3, Y4, Y5, and Y6 are independently selected from a hydrogen atom, a substituted or unsubstituted alkyl, a substituted or unsubstituted alkenyl, and a substituted or unsubstituted alkynyl.

Another aspect of the present disclosure provides an electronic apparatus including the OLED display panel.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the invention, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present invention. Based on the disclosed embodiments, persons of ordinary skill in the art may derive other embodiments consistent with the present disclosure, all of which are within the scope of the present invention. Further, in the present disclosure, the disclosed embodiments and the features of the disclosed embodiments may be combined under conditions without conflicts.

The present disclosure provides an organic light-emitting diode (OLED) display panel, comprising: a substrate; an organic light-emitting device, including a first electrode, a laminated layer comprising an organic light-emitting layer, and a second electrode, successively disposed on one side of the substrate, wherein the second electrode has a first side facing toward the substrate and an opposing side; and a capping layer disposed on the opposing side of the second electrode.

The capping layer may be formed by a material comprising a compound of the following chemical formula (I):

chemical formula (I)

where L1, L2, L3, and L4 may be independently selected from a hydrogen atom, a substituted or unsubstituted alkyl, a substituted or unsubstituted alkenyl, a substituted or unsubstituted alkynyl, and a substituted or unsubstituted phenyl. A total quantity of benzene rings included in L1, L2, L3, and L4 may be from 0 to 6. Y1, Y2, Y3, Y4, Y5, and Y6 may be independently selected from any one of a hydrogen atom, a substituted or unsubstituted alkyl, a substituted or unsubstituted alkenyl, and a substituted or unsubstituted alkynyl.

When an organic material is adopted to form the capping layer by the inkjet printing, the organic material may be deposited repeatedly in a layer-by-layer manner by the inkjet printing to form the capping layer. When the solubility of the organic material is substantially high, the organic material with the inkjet solvent may dissolve the previously deposited organic layer by the inkjet printing, causing bumps and hollows in the previously deposited organic layer. Thus the moisture and oxygen barrier properties of the capping layer may be degraded and, accordingly, the lifetime of the OLED display panel may be degraded.

In the disclosed embodiments, the compound of the chemical formula (I) may form a capping layer by the inkjet printing. Meanwhile, through configuring a desired quantity of benzene rings in the compound, the previously deposited organic layer may have a reduced solubility in the organic material with the inkjet solvent, during the inkjet printing process. Thus, the previously deposited organic layer may not be dissolved in the organic material with the inkjet solvent and, accordingly, the surface smoothness of each deposited organic layer may be improved. Thus, the moisture and oxygen barrier properties of the OLED device may be improved, and the corresponding lifetime may be extended, accordingly.

Meanwhile, through configuring the desired quantity of benzene rings in the compound, the solubility of the organic material may not be too low to be uniformly discharged from, e.g., a nozzle, during the inkjet printing process, without degrading the moisture and oxygen barrier properties of the OLED device and the corresponding lifetime.

In one embodiment, an encapsulating layer may be disposed on the capping layer, and the encapsulating layer may at least include one inorganic layer and one organic layer. Further, the material of the organic layer may comprise a compound of the chemical formula (I). By configuring the additional organic layer (i.e., the organic layer in the encapsulating layer) to include the compound of the chemical formula (I), the light transmittance of the encapsulating layer may be ensured.

The capping layer may have a first side facing toward the substrate and an opposing side. In one embodiment, the encapsulating layer may include a first inorganic layer, an organic layer and a second inorganic layer sequentially disposed on the opposing side of the capping layer.

In one embodiment, at room temperature, the compound of the chemical formula (I) may have a solubility of approximately 0.2~0.4 g/L in N-methylpyrrolidone, such as 0.21 g/L, 0.22 g/L, 0.23 g/L, 0.24 g/L, 0.25 g/L, 0.26 g/L, 0.27 g/L, 0.28 g/L, 0.29 g/L, 0.30 g/L, 0.31 g/L, 0.32 g/L, 0.33 g/L, 0.34 g/L, 0.35 g/L, 0.36 g/L, 0.37 g/L, 0.38 g/L, 0.39 g/L, etc.

In another embodiment, at room temperature, the compound of the chemical formula (I) may have a solubility of approximately 0.2~0.3 g/L in cyclohexanone, such as 0.21 g/L, 0.22 g/L, 0.23 g/L, 0.24 g/L, 0.25 g/L, 0.26 g/L, 0.27 g/L, 0.28 g/L, 0.29 g/L, 0.30 g/L, 0.31 g/L, 0.32 g/L, 0.33 g/L, 0.34 g/L, 0.35 g/L, 0.36 g/L, 0.37 g/L, 0.38 g/L, 0.39 g/L, etc.

In one embodiment, the refractive index n of the capping layer may be greater than or equal to approximately 1.5, such as 1.6, 1.7, 1.9, 2.1, 2.3, 2.5, 2.6, etc.

In one embodiment, the thickness of the capping layer may be approximately 20~150 nm, such as 21 nm, 24 nm, 26 nm, 29 nm, 31 nm, 34 nm, 36 nm, 39 nm, 41 nm, 44 nm, 46 nm, 49 nm, 51 nm, 54 nm, 56 nm, 59 nm, 61 nm, 64 nm, 66 nm, 69 nm, 71 nm, 74 nm, 76 nm, 79 nm, 81 nm, 84 nm, 86 nm, 89 nm, 91 nm, 94 nm, 96 nm, 99 nm, 101 nm, 104 nm, 106 nm, 109 nm, 111 nm, 114 nm, 116 nm, 119 nm, 121 nm, 124 nm, 126 nm, 129 nm, 131 nm, 134 nm, 136 nm, 139 nm, 141 nm, 144 nm, 146 nm, 149 nm, etc.

In one embodiment, Y1, Y2, Y3, Y4, Y5, and Y6 each may include a hydrogen, and L1, L2, L3, and L4 each may include a phenyl.

In one embodiment, the thickness of the inorganic layer in the encapsulating layer may be approximately 700~1000 nm, such as 710 nm, 740 nm, 760 nm, 790 nm, 810 nm, 840 nm, 860 nm, 890 nm, 910 nm, 940 nm, 960 nm, 990 nm, etc.

In one embodiment, the thickness of the organic layer in the encapsulating layer may be approximately 7000~8000 nm, such as 7100 nm, 7200 nm, 7300 nm, 7400 nm, 7500 nm, 7600 nm, 7700 nm, 7800 nm, 7900 nm, etc.

In one embodiment, the compound of the chemical formula (I) may include one or a combination of at least two selected from the following:

-continued

, and

In one embodiment, the inorganic layer of the encapsulating layer may be formed by a material including one or a combination of at least two selected from a metal oxide, a metal nitride, a metal carbide, and a metal oxynitride. That is, the material of the inorganic layer of the encapsulating layer may include at least one of a metal oxide, a metal nitride, a metal carbide, and a metal oxynitride.

In another embodiment, the inorganic layer of the encapsulating layer may be formed by a material including a silicon nitride or $Al_2O_3$.

In one embodiment, the capping layer may be formed by the inkjet printing.

In one embodiment, the organic layer of the encapsulating layer may be formed by the inkjet printing.

Figure 3:
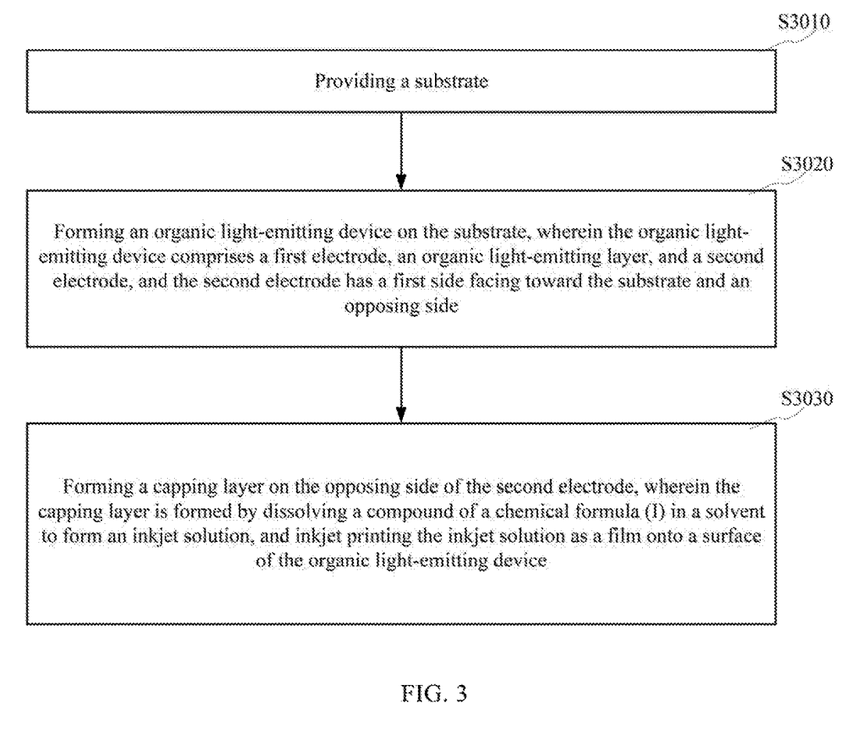
FIG. 3 illustrates a flow chart of an exemplary OLED display panel fabrication method consistent with disclosed embodiments.
Figure 4:
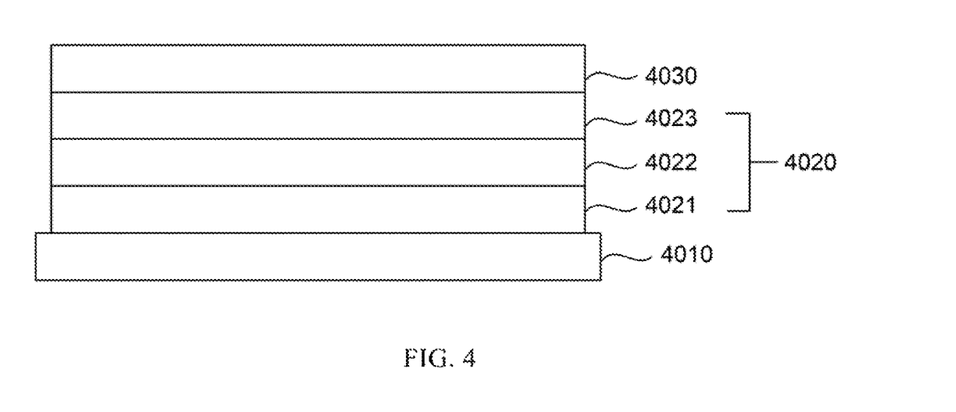
FIG. 4 illustrates a cross-sectional view of an exemplary OLED panel during certain stages of the fabrication method in FIG. 3 consistent with disclosed embodiments.

The present disclosure may also provide a fabrication method for an OLED display panel. FIG. 3 illustrates a flow chart of an exemplary OLED display panel fabrication method consistent with disclosed embodiments. FIG. 4 illustrates a cross-sectional view of an exemplary OLED panel during certain stages of the fabrication method in FIG. 3 consistent with disclosed embodiments.

As shown in FIG. 3, the OLED display panel fabrication method may include following steps.

At the beginning, a substrate is provided (S3010). As shown in FIG. 4, a substrate 4010 may be provided. The substrate 4010 may be a rigid substrate or a flexible substrate.

Returning to FIG. 3, after the substrate is provided, an organic- light-emitting device is formed on the substrate (S3020). As shown in FIG. 4, an organic light-emitting device 4020 may be formed on the substrate 4010. The organic light-emitting device 4020 may include a first electrode 4021, a laminated layer comprising an organic light-emitting layer 4022, and a second electrode 4023. The second electrode 4023 may have a first side facing toward the substrate 4010 and an opposing side.

Returning to FIG. 3, after the organic light-emitting device is formed on the substrate, a capping layer is disposed on the opposing side of the second electrode (S3030). As shown in FIG. 4, a capping layer 4030 may be disposed on the opposing side of the second electrode 4023. The capping layer 4030 may be formed by inkjet printing an inkjet solution as a film onto the surface of the organic light-emitting device 4020, in which the inkjet solution may be formed by dissolving a compound of a chemical formula (I) in a solvent.

The compound may have the following chemical formula (I):

chemical formula (I)

where L1, L2, L3, and L4 may be independently selected from a hydrogen atom, a substituted or unsubstituted alkyl, a substituted or unsubstituted alkenyl, a substituted or unsubstituted alkynyl, and a substituted or unsubstituted phenyl, and a total quantity of benzene rings included in L1, L2, L3, and L4 may be from 0 to 6, and Y1, Y2, Y3, Y4, Y5, and Y6 may be independently selected from a hydrogen atom, a substituted or unsubstituted alkyl, a substituted or unsubstituted alkenyl, and a substituted or unsubstituted alkynyl.

In one embodiment, an encapsulating layer may be formed after forming the capping layer; and the encapsulating layer may include at least one inorganic layer and at least one organic layer. That is, the encapsulating layer may be formed on the capping layer.

In one embodiment, the organic layer may be formed by inkjet printing the inkjet solution as a film onto the surface of the organic light-emitting device, in which the inkjet solution may be formed by dissolving a compound of the chemical formula (I) in a solvent.

In one embodiment, the solvent may include at least one of N-methylpyrrolidone and cyclohexanone.

In one embodiment, Y1, Y2, Y3, Y4, Y5, and Y6 each may include a hydrogen, and L1, L2, L3, and L4 each may include a phenyl.

Figure 1:
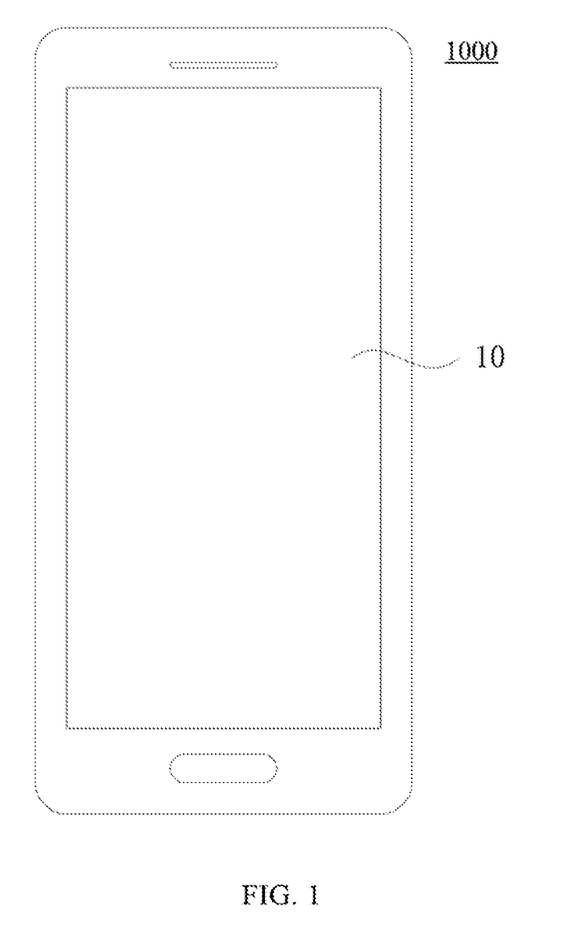
FIG. 1 illustrates a schematic view of an exemplary electronic apparatus consistent with disclosed embodiments.

The present disclosure also provides an electronic apparatus including any one of the disclosed OLED display panels. FIG. 1 illustrates a schematic view of an exemplary electronic apparatus consistent with disclosed embodiments.

As shown in FIG. 1, the electronic apparatus 1000 may include an OLED display panel 10, which may be any one of the disclosed OLED display panels 10. The disclosed electronic apparatus may be a cell phone as shown in FIG. 1, a tablet, a computer, a TV, a monitor, and a smart wearable display apparatus, etc. Any electronic apparatus comprising any one of the disclosed OLED display panels will fall within the scope of the present disclosure. Although a cell phone is shown in FIG. 1, the disclosed electronic apparatus is not limited to the cell phone.

In the disclosed embodiments, a compound of the chemical formula (I) may be synthesized by existing technologies. An exemplary synthetic route for an exemplary compound may include the following procedures:

In the chemical formula (I) according to the present disclosure, the substituents L1, L2, L3, L4, Y3, Y4, Y5, and Y6 may be introduced by selectively introducing phenol. For example, to introduce L1, excess phenol having an L1 group may be added, and to introduce Y1, excess phenol having a Y1 group may be added.

Figure 2:
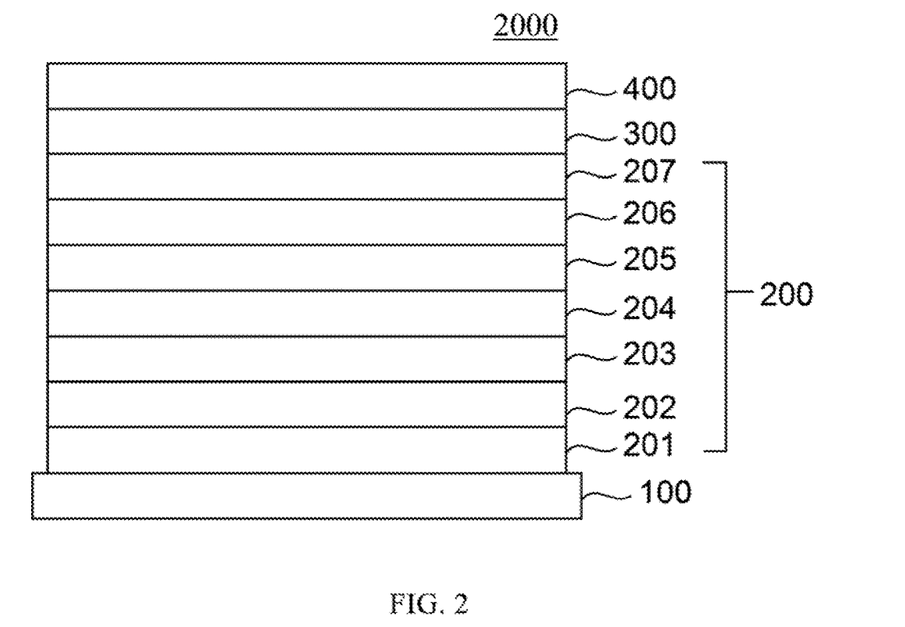
FIG. 2 illustrates a schematic view of an exemplary organic light-emitting diode (OLED) display panel consistent with disclosed embodiments.

FIG. 2 illustrates a schematic view of an exemplary OLED display panel consistent with disclosed embodiments.

As shown in FIG. 2, the OLED display panel 2000 may include: a substrate 100; an organic light-emitting device 200 disposed on one side of the substrate; a capping layer 300 disposed on the organic light-emitting device 200; and an encapsulating layer 400 disposed on the capping layer 300. In particular, the organic light-emitting device 200 may include a first electrode (e.g. indium tin oxide (ITO) electrode) 201, a hole injection layer 202, a hole transport layer 203, a light-emitting layer 204, an electron transport layer 205, an electron injection layer 206, and a second electrode 207 successively disposed on one side of the substrate. The second electrode 207 may have a first side facing toward the substrate 100 and an opposing side, and the capping layer 300 may be disposed on the opposing side of the second electrode 207. In another embodiment, the organic light-emitting device 200 may also include other appropriate layers.

The thickness of the light-emitting layer 204 may be approximately 30~65 nm. For example, the light-emitting layer 204 may include a blue light-emitting layer, a red light-emitting layer and a green light-emitting layer. In another embodiment, the light-emitting layer 204 may include light-emitting layers for emitting additional primary light, or secondary light of an additional and/or different color than the red, green and blue light (e.g., yellow light, or a different shade of red or green or blue light).

The blue light-emitting layer may include fluorescent or phosphorescent materials. In one-embodiment, the blue light-emitting layer may include an iridium (Ir) derivative, such as bis(fluorophenylpyridine) picolinatoiridium. In another embodiment, the blue light-emitting layer may include an anthracene derivative, such as diphenylanthracene. In another embodiment, the blue light-emitting layer may include a styrylbenzene derivative, such as 4,4'-bis(diphenylamino) 1,2-diphenylethylene. In one embodiment, the red light-emitting layer may include bis(phenylisoquinoline) acetylacetonato iridium. In one embodiment, the green light-emitting layer may include tris(phenylpyridine) iridium.

The hole transport layer 203 may have a thickness of 15~45 nm approximately. In one embodiment, the material of the hole transport layer 203 may be selected from 1,3,5-tris(carbazolyl) benzene, 4,4'-bis(carbazolyl) biphenyl, 4,4'-bis(carbazolyl)-2,2'-dimethyl biphenyl, 4,4',4'',-tris (N-carbazolyl) triphenylamine, 1,3,5-tris(2-carbazolylphenyl) benzene, 1,3,5-tris(2-carbazolyl-5-methoxyphenyl) benzene, etc.

The electron transport layer 205 may have a thickness of 20~60 nm approximately. In one embodiment, the material of the electron transport layer 205 may be selected from bis(8-hydroxyquinoline) biphenoxy aluminum, bis(8-hydroxyquinoline) phenoxy aluminum, bis(2-methyl-8-hydroxyquinoline) biphenoxy aluminum, bis(2-methyl-8-hydroxyqiunoline) phenoxy aluminum, bis(2-(2-hydroxyphenyl) qiunoline) zinc, 10-phenanthroline (i.e. bathocuproine, BCP), 2,4,6-tris(diarylamino)-1,3,5-triazine, 3-phenyl-4-(1'-naphthyl)-5-phenyl-1,2,4-triazole, etc.

The hole injection layer 202 may have a thickness of 40~150 nm approximately. The material of the hole injection layer 202 may be selected from copper phthalocyanine (CuPc) or starburst amine, such as TCTA (4,4',4''-tris(carbazol-9-yl) triphenylamine), and m-MTDATA (4,4,4-tris(N-3-methylphenyl-N-phenylamino) triphenylamine).

The electron injection layer 206 may have a thickness of 10~20 nm approximately. The material of the electron injection layer 206 may be selected from LiF, CsF, $Li_2O$, BaO, etc. In certain embodiments, the material of the second electrode 207 may be selected from Mg, Al, Mg—In, Mg—Ag, Al—Li, etc.

The capping layer 300 may have a thickness of approximately 20~150 nm. The material of the capping layer 300 may include a compound of a chemical formula (I). The encapsulating layer 400 may include an inorganic layer disposed on the capping layer 300 and an organic layer.

In one embodiment, the inorganic layer may be made of SiNx, and may have a thickness of approximately 800 nm. The organic layer may be made of and have a thickness of approximately 7200 nm. The material of the organic layer may be selected from NPB (N,N'-bis(1-naphthyl)-N,N'-diphenyl-1,1'-diphenyl-4,4'-diamine), CBP (4,4'bis(carbazol-9-yl) biphenyl), TCTA (4,4',4''-tris(carbazol-9-yl) triphenylamine), m-MTDATA (4,4,4-tris(N-3-methylphenyl-N-phenylamino) triphenylamine), etc.

The present disclosure also provides comparative performance tests on various exemplary OLED display panels consistent with disclosed embodiments and reference OLED display panels.

The test methods may include:
(1) measuring the solubility of the compound adopted in the capping layer, where the test method may include: testing samples with different concentrations of the compound by Ultimate3000 liquid chromatographic instrument manufactured by company "waters", plotting a standard curve, then testing a saturated solution, and calculating the solubility by combining the standard curve;
(2) measuring light extraction efficiency by an UVISEB ellipsometer from HORIBA (China) Trading Co., Ltd.; and
(3) measuring lifetime by a LTS-1004DC life tester with from supplier ENC.

Based on the structure of the OLED display panel shown in FIG. 2, the exemplary OLED display panels 1 to 9 and reference OLED display panels 1 to 3 are provided.

As shown in FIG. 2, the OLED display panel may include: a substrate 100; an organic light-emitting device 200 disposed on one side of the substrate 100; a capping layer 300 disposed on the organic light-emitting device 200; and an encapsulating layer 400 disposed on the capping layer 300. In particular, the organic light-emitting device 200 may include a first electrode (e.g. indium tin oxide (ITO) electrode) 201, a hole injection layer 202, a hole transport layer 203, a light-emitting layer 204, an electron transport layer 205, an electron injection layer 206, and a second electrode 207 successively disposed on one side of the substrate 100. The second electrode 207 may have a first side facing toward the substrate 100 and an opposing side, and the capping layer 300 may be disposed on the opposing side of the second electrode 207.

The thickness of the light-emitting layer 204 may be approximately 45 nm. The host material in the red light region may include AlQ (8-hydroxyquinoline aluminum), doped with bis(phenylisoquinoline) acetylacetone iridium at a volume ratio of approximately 5%. The host material in the blue light region may include MADN (9,10-bis(2-naphthyl)-2-methyl anthracene; 2-methyl-9,10-bis(2-naphthyl) anthracene; 2-methyl-9,10-bis(naphthalen-2-yl) anthracene), doped with 4,4'-bis(di-phenylamino) 1,2-diphenylethene at a volume ratio of approximately 3%. The host material of the green light region may include quinacridone, doped with tris(phenylpyridine) iridium at a volume ratio of approximately 10%.

The hole transport layer 203 may include L3,5-tris(carbazolyl) benzene. The host material of the hole injection layer 202 may include copper phthalocyanine (CuPc), doped with 2,3,5,6-tetrafluoro-7,7,8,8-tetracyanoquinodimethane at a volume ratio of approximately 5%. The host material of the electron transport layer 205 may include BPHEN (bathophenanthroline), doped with $Liq_3$ at a volume ratio of approximately 50%. The electron injection layer 206 may include LiF. The material of the second electrode 207 may include Mg. The encapsulating layer 400 may include an inorganic layer of SiNx having a thickness of approximately 800 nm, and an organic layer having a thickness of approximately 7200 nm, disposed on the capping layer 300. The material configurations of the capping layer 300 are shown in Table 1 (the $1^{st}$-$9^{th}$ exemplary OLED display panels) and Table 2 (the $1^{st}$-$3^{rd}$ reference OLED display panels 1 to 3). The thickness of the capping layer 300 may be approximately 70 nm. The organic layer of the encapsulating layer 400 may have the same material as the capping layer 300.

Table 1 shows the test results of the $1^{st}$-$9^{th}$ exemplary OLED display panels.

TABLE 1

Materials of the capping layer and performance test results of the $1^{st}$-$9^{th}$ exemplary OLED display panels

| No. | Material of capping layer | Solubility | Light extraction efficiency | Lifetime |
|---|---|---|---|---|
| $1^{st}$ exemplary OLED display panel | [structure] | 0.210 g/l | 73% | 820 h |
| $2^{nd}$ exemplary OLED display panel | [structure] | 0.205 g/l | 76% | 828 h |
| $3^{rd}$ exemplary OLED display panel | [structure] | 0.312 g/l | 65% | 761 h |

TABLE 1-continued

Materials of the capping layer and performance test results of the 1st-9th exemplary OLED display panels

| No. | Material of capping layer | Solubility | Light extraction efficiency | Lifetime |
|---|---|---|---|---|
| 4th exemplary OLED display panel | [structure] | 0.309 g/l | 67% | 775 h |
| 5th exemplary OLED display panel | [structure] | 0.211 g/l | 71% | 803 h |
| 6th exemplary OLED display panel | [structure] | 0.210 g/l | 73% | 819 h |

TABLE 1-continued

Materials of the capping layer and performance test results of the 1st-9th exemplary OLED display panels

| No. | Material of capping layer | Solubility | Light extraction efficiency | Lifetime |
|---|---|---|---|---|
| 7th exemplary OLED display panel |  | 0.340 g/l | 62% | 748 h |
| 8th exemplary OLED display panel |  | 0.300 g/l | 69% | 780 h |
| 9th exemplary OLED display panel |  | 0.298 g/l | 70% | 792 h |

The 1st-3rd reference OLED display panels have the same structure as the 1st-9th exemplary OLED display panels, except for the different materials of the capping layer 300 as shown in Table 2.

The disclosed capping layer may have a suitable solubility to provide a smooth surface when fabricating the capping layer by inkjet printing, and effectively prevent the intrusion of moisture and oxygen in the fabrication process. Accord-

TABLE 2

Materials of the capping layer and performance test results of the 1st-3rd reference OLED display panels

| No. | material of capping layer | solubility | light extraction efficiency | lifetime |
|---|---|---|---|---|
| 1st reference OLED display panel | LiF | 0 | 46% | 762 h |
| 2nd reference OLED display panel | [chemical structure: biphenyl-based diamine with cyclohexyl, methyl, and n-butyl substituents] | 0.566 g/l | 55% | 603 h |
| 3rd reference OLED display panel | [chemical structure: biphenyl-based diamine with methyl substituent and four terphenyl arms] | 0.430 g/l | 59% | 620 h |

Compared to the conventional organic materials, the inorganic layer (e.g. LiF) may have better moisture and oxygen barrier property and, accordingly, the OLED display panel may have a longer lifetime, but the light extraction efficiency may be lower. The OLED display panel, in which the organic layer is formed by the compound of an improper quantity of the benzene rings may have slightly higher light extraction efficiency than the OLED display panel including the inorganic layer. However, due to the high solubility of the organic layer formed by the compound of an improper quantity of the benzene rings, bumps and holes may be formed during the fabrication process and, accordingly, the device may be easily intruded by moisture and oxygen during the fabrication process, leading to a reduced lifetime.

ingly, the fabricated OLED display panel may have an improve lifetime and light extraction efficiency.

In another embodiment, the OLED display panel shown in FIG. 2 may include: a substrate 100; an organic light-emitting device 200 disposed on one side of the substrate; a capping layer 300 disposed on the organic light-emitting device 200; and an encapsulating layer 400 disposed on the capping layer 300. In particular, the organic light-emitting device 200 may include a first electrode (e.g. indium tin oxide (ITO) electrode) 201, a hole injection layer 202, a hole transport layer 203, a light-emitting layer 204, an electron transport layer 205, an electron injection layer 206, and a second electrode 207 successively disposed on one side of the substrate 100. The second electrode 207 may have a first side facing toward the substrate 100 and an opposing side, and the capping layer 300 may be disposed on the opposing side of the second electrode 207.

In the OLED display panel, the thickness of the light-emitting layer 204 may be approximately 45 nm. The host material of the red light region may include AlQ (8-hydroxyquinoline aluminum), doped with bis(phenylisoquinoline) acetylacetone iridium at a volume ratio of approximately 5%. The host material of the blue light region may include MADN (9,10-bis(2-naphthyl)-2-methyl anthracene; 2-methyl-9,10-bis(2-naphthyl) anthracene; 2-methyl-9,10-bis(naphthalen-2-yl) anthracene), doped with 4, 4'-bis(diphenylamino) 1,2-diphenylethene at a volume ratio of approximately 3%. The host material of the green light region may include quinacridone, doped with tris(phenylpyridine) iridium at a volume ratio of approximately 10%.

The hole transport layer 203 may include 1,3,5-tris(carbazolyl) benzene. The host material of the hole injection layer 202 may include copper phthalocyanine (CuPc), doped with 2,3,5,6-tetrafluoro-7,7,8,8-tetracyanoquinodimethane at a volume ratio of approximately 5%, The host material of the electron transport layer 205 may include BPHEN (bathophenanthroline), doped with $Liq_3$ at a volume ratio of approximately 50%. The electron injection layer 206 may include LiF.

The encapsulating layer 400 may include an inorganic layer of SiNx having a thickness of approximately 800 nm and an organic layer of NPB (N,N'-(1-naphthyl)-N,N'-diphenyl-1,1'-diphenyl-4,4'-diamine), having a thickness of approximately 7200 nm, disposed on the capping layer 300. The material of the capping layer 300 may include The thickness of the capping layer may be approximately 70 nm.

The photoelectric conversion efficiency and lifetime of the OLED display panel are measured. The measurement methods are the same as those of Table 1. According to measurements, the OLED display panel as shown in FIG. 2 shows a light extraction efficiency of approximately 66% and a lifetime of approximately 810 hours.

According to the measurement results of the $1^{st}$ to $9^{th}$ exemplary OLED display panels and the $1^{st}$ to $3^{rd}$ reference OLED display panels, the capping layer formed by a compound of the chemical formula (I) may improve the light extraction efficiency of the OLED display panel, effectively block moisture and oxygen, protect the OLED display panel from the erosion of moisture and oxygen, without degrading the lifetime of the OLED display panel.

The present disclosure provides an OLED display panel. The OLED display panel may include: a substrate; an organic light-emitting device including a first electrode, a laminated layer comprising an organic light-emitting layer, and a second electrode, successively disposed on one side of the substrate, wherein the second electrode has a first side feeing toward the substrate and an opposing side; a capping layer formed by a material comprising a compound of the chemical formula (I), wherein the capping layer is disposed on the opposing side of the second electrode. The capping layer may improve the light extraction efficiency of the OLED display panel, effectively block moisture and oxygen, and protect the OLED display panel from the erosion of moisture and oxygen. Thus, the performance and lifetime of the OLED display panel may be enhanced.

The description of the disclosed embodiments is provided to illustrate the present invention to those skilled in the art. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An organic light-emitting diode (OLED) display panel, comprising:
   a substrate;
   an organic light-emitting device comprising a first electrode, an organic light-emitting layer, and a second electrode, successively disposed on one side of the substrate, wherein the second electrode has a first side facing toward the substrate and an opposing side; and
   a capping layer disposed on the opposing side of the second electrode,
   wherein a material of the capping layer includes a compound of the following chemical formula (I):

chemical formula (I)

wherein:
   L1, L2, L3, and L4 are independently selected from a hydrogen atom, a substituted or unsubstituted alkyl, a substituted or unsubstituted alkenyl, a substituted or unsubstituted alkynyl, and a substituted or unsubstituted phenyl, and a total quantity of benzene rings included in L1, L2, L3, and L4 is from 0 to 6; and
   Y1, Y2, Y3, Y4, Y5, and Y6 include:
   two selected from Y3, Y4, Y5, and Y6, each including one of the alkenyl and the alkynyl, and
   a remaining of Y1, Y2, Y3, Y4, Y5, and Y6, being independently selected from a hydrogen atom, a substituted or unsubstituted alkyl, a substituted or unsubstituted alkenyl, and a substituted or unsubstituted alkynyl.

2. The OLED display panel according to claim 1, wherein:
   an encapsulating layer is disposed on the capping layer; and the encapsulating layer at least includes a plurality of inorganic layers and an organic layer.

3. The OLED display panel according to claim 2, wherein:
a material of the organic layer in the encapsulating layer includes the compound of the chemical formula (I).

4. The OLED display panel according to claim 2, wherein:
the capping layer has a side facing toward the second electrode and an opposing side;
the plurality of inorganic layers of the encapsulating layer include a first inorganic layer and a second inorganic layer, and
the first inorganic layer, the organic layer and the second inorganic layer are disposed successively on the opposing side of the capping layer.

5. The OLED display panel according to claim 1, wherein:
the compound of the chemical formula (I) has a solubility of approximately 0.2 g/L to 0.4 g/L in N-methylpyrrolidone at room temperature; or
the compound of the chemical formula (I) has the solubility of approximately 0.2 g/L to 0.3 g/L in cyclohexanone at room temperature.

6. The OLED display panel according to claim 1, wherein:
a refractive index n of the capping layer is greater than or equal to approximately 1. 5.

7. The OLED display panel according to claim 1, wherein:
a thickness of the capping layer is approximately 20 nm to 150 nm.

8. The OLED display panel according to claim 2, wherein:
a thickness of the inorganic layer in the encapsulating layer is approximately 700 nm to 1000 nm.

9. The OLED display panel according to claim 2, wherein:
a thickness of the organic layer in the encapsulating layer is approximately 7000 nm to 8000 nm.

10. The OLED display panel according to claim 1, wherein the material of the capping layer further includes:

11. The OLED display panel according to claim 2, wherein:
a material of the inorganic layer in the encapsulating layer includes at least one of a metal oxide, a metal nitride, a metal carbide, and a metal oxynitride.

12. The OLED display panel according to claim 2, wherein:
a material of the inorganic layer of the encapsulating layer includes silicon nitride or $Al_2O_3$.

13. The OLED display panel according to claim 1, wherein:
the capping layer is formed by inkjet printing.

14. The OLED display panel according to claim 3, wherein: the organic layer in the encapsulation layer is formed by inkjet printing.

15. An electronic apparatus, comprising the OLED display panel according to claim 1.

16. An organic light-emitting diode (OLED) display panel, comprising:
a substrate;
an organic light-emitting device comprising a first electrode, an organic light-emitting layer, and a second electrode, successively disposed on one side of the substrate, wherein the second electrode has a first side facing toward the substrate and an opposing side; and
a capping layer disposed on the opposing side of the second electrode,
wherein a material of the capping layer includes a compound of the following chemical formula (I):

chemical formula (I)

wherein:
Y1, Y2, Y3, Y4, Y5 and Y6 include:
two selected from Y3, Y4, Y5, and Y6, each including one of the alkenyl and the alkynyl, and
a remaining of Y1, Y2, Y3, Y4, Y5, and Y6, each including a hydrogen; and
L1, L2, L3 and L4 each includes a phenyl.

17. A fabrication method for an OLED display panel, comprising:
providing a substrate;
forming an organic light-emitting device on the substrate, wherein the organic light-emitting device comprises a first electrode, an organic light-emitting layer, and a second electrode, and the second electrode has a first side facing toward the substrate and an opposing side; and
forming a capping layer on the opposing side of the second electrode, wherein the capping layer is formed by dissolving a compound of the following chemical formula (I) in a solvent to form an inkjet solution, and inkjet printing the inkjet solution as a film onto a surface of the organic light-emitting device, chemical formula (I)

wherein:
L1, L2, L3, and L4 are independently selected from a hydrogen atom, a substituted or unsubstituted alkyl, a substituted or unsubstituted alkenyl, a substituted or unsubstituted alkynyl, and a substituted or unsubstituted phenyl, and a total quantity of benzene rings included in L1, L2, L3, and L4 is from 0 to 6;
Y1, Y2, Y3, Y4, Y5, and Y6 include:
  two selected from Y3, Y4, Y5, and Y6, each including one of the alkenyl and the alkynyl, and
  a remaining of Y1, Y2, Y3, Y4, Y5, and Y6, being independently selected from a hydrogen atom, a substituted or unsubstituted alkyl, a substituted or unsubstituted alkenyl, and a substituted or unsubstituted alkynyl.

18. The fabrication method according to claim 17, further including:
forming an encapsulating layer on the capping layer,
wherein the encapsulating layer includes at least one inorganic layer and at least one organic layer.

19. The fabrication method according to claim 18, wherein the at least one organic layer is formed by:
dissolving the compound of the chemical formula (I) in a solvent to form an inkjet solution, and
inkjet printing the inkjet solution to form a film.

20. The fabrication method according to claim 17, wherein:
the solvent includes at least one of N-methylpyrrolidone and cyclohexanone; and
L1, L2, L3, and L4 each includes a phenyl.

21. An organic light-emitting diode (OLED) display panel, comprising:
a substrate;
an organic light-emitting device comprising a first electrode, an organic light-emitting layer, and a second electrode, successively disposed on one side of the substrate, wherein the second electrode has a first side facing toward the substrate and an opposing side; and
a capping layer disposed on the opposing side of the second electrode, wherein a material of the capping layer includes at least one of:

and

* * * * *